US011351029B2

(12) United States Patent
Elibol

(10) Patent No.: US 11,351,029 B2
(45) Date of Patent: Jun. 7, 2022

(54) MEASUREMENT AND SIMULATION DEVICE USED FOR AORTIC VALVE-SPARING ROOT REPLACEMENT OPERATIONS

(71) Applicant: Ahmet Elibol, Istanbul (TR)

(72) Inventor: Ahmet Elibol, Istanbul (TR)

( * ) Notice: Subject to any disclaimer, the term of this patent is extended or adjusted under 35 U.S.C. 154(b) by 498 days.

(21) Appl. No.: 16/467,204

(22) PCT Filed: Nov. 29, 2017

(86) PCT No.: PCT/TR2017/050610
§ 371 (c)(1),
(2) Date: Jun. 6, 2019

(87) PCT Pub. No.: WO2019/054961
PCT Pub. Date: Mar. 21, 2019

(65) Prior Publication Data
US 2020/0085581 A1 Mar. 19, 2020

(30) Foreign Application Priority Data

Dec. 9, 2016 (TR) .................................. 2016 18240

(51) Int. Cl.
A61F 2/24 (2006.01)
A61B 90/00 (2016.01)
(Continued)

(52) U.S. Cl.
CPC ........ A61F 2/2496 (2013.01); A61B 17/0482 (2013.01); A61B 2017/00243 (2013.01); A61B 2017/0406 (2013.01); A61B 2017/0414 (2013.01); A61B 2017/0464 (2013.01); A61B 2090/061 (2016.02); A61B 2090/08021 (2016.02); A61F 2250/001 (2013.01)

(58) Field of Classification Search
CPC ........ A61F 2/24; A61F 2/2412; A61F 2/2427; A61F 2/2445; A61F 2/2496; A61F 2090/061; A61F 2250/001; A61F 2/243; A61F 2/2442; A61B 90/06; A61B 2090/061
See application file for complete search history.

(56) References Cited

U.S. PATENT DOCUMENTS 6,494,889 B1  12/2002  Fleischman et al.
2002/0020074 A1*  2/2002  Love .................... A61B 5/1076
                                                        33/512

(Continued)

FOREIGN PATENT DOCUMENTS

WO    9730659 A1    8/1997
WO    2015077599 A1    5/2015

OTHER PUBLICATIONS

International Search Report and Written Opinion of the International Searching Authority issued in PCT/TR2017/050610; dated Apr. 29, 2019; ISA/TR.

Primary Examiner — Martin T Ton
(74) Attorney, Agent, or Firm — Harness, Dickey & Pierce, P.L.C.

(57) ABSTRACT

This invention is related to the device used in the valve sparing aortic root replacement which is a special operation aimed at the root of the main vessel—aorta originating from the heart or known as 'David Procedure' (Re-implantation technique) in the literature.

15 Claims, 7 Drawing Sheets

(51) Int. Cl.
   *A61B 17/04* (2006.01)
   *A61B 17/00* (2006.01)

(56) References Cited

U.S. PATENT DOCUMENTS

| | | | |
|---|---|---|---|
| 2009/0299469 A1 | 12/2009 | Kollar | |
| 2010/0217092 A1* | 8/2010 | Paolitto | A61B 90/06 600/235 |
| 2014/0107774 A1* | 4/2014 | Dobrilovic | A61F 2/2496 623/2.41 |
| 2014/0371842 A1* | 12/2014 | Marquez | A61F 2/2445 623/2.11 |
| 2016/0015513 A1* | 1/2016 | Lashinski | A61F 2/2463 623/2.37 |
| 2019/0015191 A1* | 1/2019 | Berdajs | A61F 2/2412 |
| 2019/0282360 A1* | 9/2019 | Colavito | F16K 15/147 |

* cited by examiner

MEASUREMENT AND SIMULATION DEVICE USED FOR AORTIC VALVE-SPARING ROOT REPLACEMENT OPERATIONS

CROSS REFERENCE TO RELATED APPLICATIONS

This application is a U.S. National Phase Application under 35 U.S.C. 371 of International Application No. PCT/TR2017/050610 filed on Nov. 29, 2017, which claims the benefit of priority from Turkish Patent Application No. TR 2016 18240 filed Dec. 9, 2016. The entire disclosures of all of the above applications are incorporated herein by reference.

TECHNICAL FIELD

This invention is related to a novel device that can be used in valve-sparing aortic root replacement surgery, known as the 'David Procedure' (re-implantation technique), which is a special operation for the root of the aorta, the main vessel originating from the heart.

BACKGROUND OF THE INVENTION

In heart surgery, the traditional treatment method for aortic valve insufficiency due to aortic root dilatation or dissection is to replace the aorta with an artificial vessel (graft) and to replace the aortic leaflets (which may be structurally normal) with a mechanical aortic valve.

However, this mechanical valve can never meet the physiological properties of the natural valve. The patient will always be at risk for bleeding, which is one of the most important side effects of life-long anticoagulant medication. The dose of the medication is adjusted on an individual basis, requiring at least a monthly patient visit to hospital.

In case the medication dose is below the efficacy level, clot formation may occur on the metal valve, which may then rupture and result in embolism (obstruction of an artery).

The sparing of the patient's own aortic leaflets eliminates the risk of such life-long complications. The David procedure aims to preserve the patient's aortic valve. However, it can only be performed by a limited number of cardiovascular surgeons since it requires advanced experience and technical skills. The device provides the most important parameters for the success of this technique by measuring the necessary data independent of the surgeon and in compliance with the literature.

One of the most important steps of this operation is the selection of the size (diameter) of the artificial vessel (graft) appropriate for the patient. There are many methods for this selection. Therefore, it is still far from standardization and remains mainly at the discretion of the operating surgeon.

The sizing of the graft, appropriate in diameter for the patient, is of utmost importance to achieve an optimal coaptation of the aortic leaflets and to avoid postoperative aortic insufficiency. A graft of smaller than optimal size results in prolapse (collapse) with ensuing aortic regurgitation, while selection of a larger graft results in central aortic regurgitation.

In one of the approaches in the application of David Procedure, the artificial vessel diameter determination techniques to be used as compatible with the patient are defined as follows:

The first step in choosing the right size of the graft is the measurement of the aortic annulus. Several methods have been described for this measurement including:

- Measurement of the aortic annulus with preoperative and intraoperative echocardiography (an indirect method)
- Measurement of the aortic annulus with pre-operative computed tomography (an indirect method)
- Measurement with a HEGAR rod (graft diameter is determined by adding 4 mm to the diameter of the appropriately fitting rod)
- Measurement with a mechanical valve sizer (valve sizer is seated around the annulus)
- Measurement with a biological valve sizer (graft diameter is determined by adding 4 mm to the diameter of the sizer which is fully inserted into the aortic annulus)
- Measurement of the commissure height, which is equal to the diameter of the graft)

As can be understood from the related literature, there are various methods to measure the aortic annulus. The purpose of the measurement is to determine the diameter of the artificial vessel (graft) to be used. So far, none of these measurement techniques has been shown to be superior to another.

Differences between these techniques make the selection difficult. It is also difficult to determine which method is better or more accurate. Thus, due to the lack of standardization of these techniques, the choice of an appropriate technique depends largely on the experience, skills, and individual preference of the surgeon.

Again, it is reported in the literature that, since the determination of the diameter of the artificial vessel to be used for each patient is complex and subjective in these operations, 'the height measured from the three-dimensional structure of the aortic valve (inter-leaflet triangle height) would provide the diameter of the graft to be used.'

Considering that there is a difference of 2 mm between each graft diameter (26, 28, 30, 32, 34 mm), the lowest points of the leaflets (non-coronary and left coronary leaflets) are manually marked using a marker pen and the base of the triangle is drawn.

It may be estimated that there may be millimetric differences due to the distribution of the ink in the tissues and that measuring from the lower edge or the top edge of the marking would yield different graft diameter results. This measurement involves determination of the artificial vessel without observing or simulating the positioning of the aortic valve leaflets in relation to each other. As the measurement line is generated manually, it is drawn under eyeball estimate. These individual approaches would give rise to diverse measurement results.

The Aortic Caliper (Caliper for aortic valve cusps MSS-1 and MSS-2) device measures the height (effective height) of the free edges of the aortic leaflets from their bases. It is stated in the literature that this distance must be 9 mm for surgical success. The caliper only measures this height, but for a precise measurement, the surgeon must position this device accurately perpendicular to the ventriculoaortic plane (the plane just below the aortic valves).

Thus, the positioning of the device is completely surgeon-dependent. It is obvious that, as the positioning is done manually and under eyeball estimate, any deviation in perpendicular positioning will lead to inaccurate measurement. Objectivity of this measurement has been a matter of debate even at scientific meetings.

The most important problem encountered in performing the procedure is that aortic regurgitation continues due to the fact that an artificial vessel, the diameter of which has been measured inaccurately, and unable to coapt at the correct configuration. As a consequence, the operation turns out to be a mechanical aortic valve replacement surgery.

In the current approach, it is attempted to position the aortic valve in the artificial vessel spatially after the artificial vessel is placed at the aortic root and sutured. Incorrect graft selection significantly reduces the success of such positioning.

Again, in a technique that is used in the literature, the application time is left to individual approach since it is a method that leaves separate measurements and preparation of grafts as compatible with those measurements for each patient to the experience and skill of the surgeon. In that sense, it is not a standardized approach.

Since the sutures are not aligned on a smooth plane under the three leaflets of the aortic valve, they need to be sutured at different heights on the inner surface of the artificial vessel (graft).

Errors made at this step cause the inability to suture the valve commissures at the same height in the artificial vessel and as a consequence, the inability of the three leaflets to coapt appropriately. The alignment of the sutures under the aortic valve is unique to the anatomy of each patient.

Although there are approaches as aimed to determine the points there these sutures correspond to in the artificial vessel, the surgeon has to make the measurements separately for each patient since the values are patient-specific and thus the approach cannot be standardized.

Each stage of the David procedure necessitates an advanced technical approach. A standardized method is not yet available due to many technical approaches and application difficulties.

In the European patent document, with document publication number EP1994913B1, available in the literature, it is expressed that "The invention essentially is related with the device used to fix and anchor valve prosthesis that are composed of interconnected wire-like elements. Due to the intended function, such the device should be implanted into the aorta at minimum invasiveness by folding it compactly and then opening it at the implantation site. In this context, it is necessary to ensure a safe adhesiveness against the aortic wall and also a safe insulation. In order to achieve this intended function, three same suspension (=curved holder piece) rigid joints, which have been aligned by offsetting each with an angle of 120°, have been interconnected as aimed to fix and support an aortic valve prosthesis. The rigid joints perform the same function as swing bearings."

The above-mentioned application refers to the device for the fixation and anchoring of aortic valve prosthesis.

In the literature, the European patent document, with document publication number EP1848375B1, it is expressed that "The invention is related with catheters that allow the implantation of cardiac valve prosthesis, especially the minimal-invasive implantation of cardiac valve prosthesis, and used for transvascular implantation with self-expanding anchor supports (=stents). The invention is aimed to reduce the patient risk during the implantation operation. In this context, a cardiac valve prosthesis equipped with anchor support, in compliance with the invention, has been placed inside a cartridge unit temporarily, as folded during the implantation operation. The cartridge unit can be fixed to a guide system at the proximal position. The guide system is equipped with a flexible section in order to be applied into an aorta. Operating elements have been inserted inside the hollow guide system. With these elements, the pieces of the cartridge units can be moved radially around their axes and/or laterally in the proximal direction. In fact, the individual parts of the anchor support can be released sequentially with the cardiac valve prosthesis."

In the referred application, the transvascular implantation of cardiac valve prostheses are performed via catheter systems.

Due to the mentioned above disadvantages in the aortic valve sparing root replacement procedures, there is a need for an aortic root replacement device used as a new cardiac valve protector.

DESCRIPTION OF THE INVENTION

The purpose of the invention is to present a valve protective aortic root replacement device that eliminates the possible disadvantages.

Another purpose of the invention is to present an approach that allows the surgeon to obtain more reliable and accurate patient data during the David Procedure, which is a difficult procedure technically.

Another purpose of the invention is to present an approach that does not force the surgeon to choose a method, as it acquires the data on patient basis.

Another purpose of the invention is to present an approach that prevents the surgeon from not performing the David Procedure.

Another purpose of the invention is to present an approach that allows the procedure to be performed in larger numbers.

Another purpose of the invention is to present an approach that reduces the total operation time by reducing the time spent by the surgeon to choose and perform a certain method among a large number of methods.

Another advantage of the invention is to present an approach that the device can be sterilized and used over and over since it is fully made of metal.

Another advantage of the invention is to present an approach that eliminates additional costs since it does not require consumables as separate for each patient.

REFERENCE NUMBERS

Figure 1:
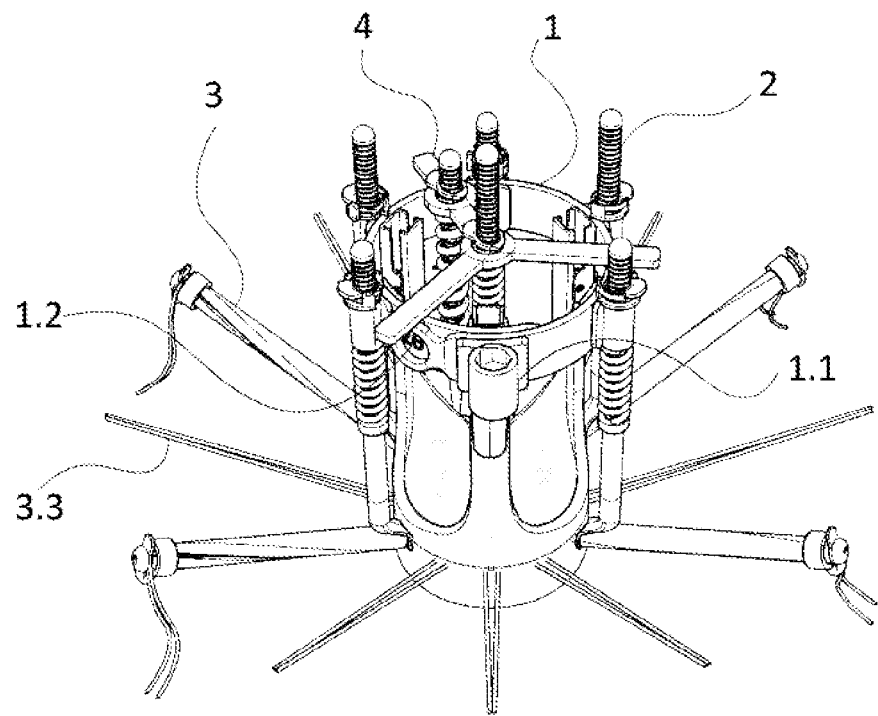
FIG. 1 Perspective view of the invention subject valve protective aortic root replacement device FIG. 2 Top view of the invention subject valve protective aortic root replacement device FIG. 3 Side view of the invention subject valve protective aortic root replacement device FIG. 4 Disassembled view of the invention subject valve protective aortic root replacement device FIG. 5 Perspective view of the commissure holders in the invention subject valve protective aortic root replacement device FIG. 6 Disassembled view of the commissure holders of the invention subject valve protective aortic root replacement device FIG. 7 Perspective view of the window showing the graft diameter scale on the invention subject valve protective aortic root replacement device FIG. 8 Disassembled view of the window showing the graft diameter scale on the invention subject valve protective aortic root replacement device FIG. 9 Detailed view of the invention subject valve protective aortic root replacement device FIG. 10 Detailed view of the invention subject valve protective aortic root replacement device FIG. 11 Disassembled view of the screw of the adjustable diameter ring on the invention subject valve protective aortic root replacement device FIG. 12 Detailed view of the measuring legs on the invention subject valve protective aortic root replacement device FIG. 13 Another perspective view of the invention subject valve protective aortic root replacement device

1. Adjustable circle
   1.1 Circle Screw
   1.2 Window showing graft diameter
   1.3 Commissure holders
2. Legs
   2.1 Support Element
   2.2 Leg stabilizer clips
   2.3 Clip stabilizers
   2.4 Leg springs
   2.5 Suture holes
   2.6 Leg connectors
3. Slit surgical tubes
   3.1 Surgical teflon pledget
   3.2 Surgical tube stopper
   3.3 Operation Suture
4. Cusp caliper (effective height caliper)
   4.1 Cusp caliper pins
   4.2 Cusp caliper clips
   4.3 Pin-pulling springs
   4.4 Pin endings
5. Functional Aortic Annulus
   5.1 Aortic commissure
   5.2 Aortic Leaflet

DETAILED DESCRIPTION OF THE INVENTION

In this detailed description, the invention subject innovation is explained by examples that will not create any limiting effects, solely as aimed for the subject to be understood better.

The invention is the valve sparing aortic root replacement device used in the operation for valve sparing aortic root replacement, which is a special operation aimed for the root of the main aorta exiting from the heart, or known as the 'David Procedure' in the literature, and its feature is characterized by; an adjustable circle (1) that determined the graft diameter with the circle screw (1.1) located on it, legs (2) connected to the referred adjustable circle (1) that are clamped on the referred aortic root and allow the placement of the valve sparing aortic root replacement device on the aortic root, slit surgical tube (3) that can hold the operation suture (3.3) that is passed through the aortic root without cutting the needles and prevent the unintended escape of the referred operation suture (3.3) thanks to the spiral slit on it that extends from end to end, surgical tube stopper (3.2) that wraps the output end of the referred operation suture (3.3) from the outside and forms a support, and the cusp caliper (effective height caliper) (4) that is placed on the top edge of the referred adjustable circle (1) and ensures the positioning of the pin ending (4.4) on it as perpendicular to the aortic root under all positions, and allows the measurement of the height difference between the lowest and highest levels of the aortic leaflets (5.2) with a totally geometric approach.

The perspective view of the invention subject valve sparing aortic root replacement device is illustrated in FIG. 1.

Figure 2:
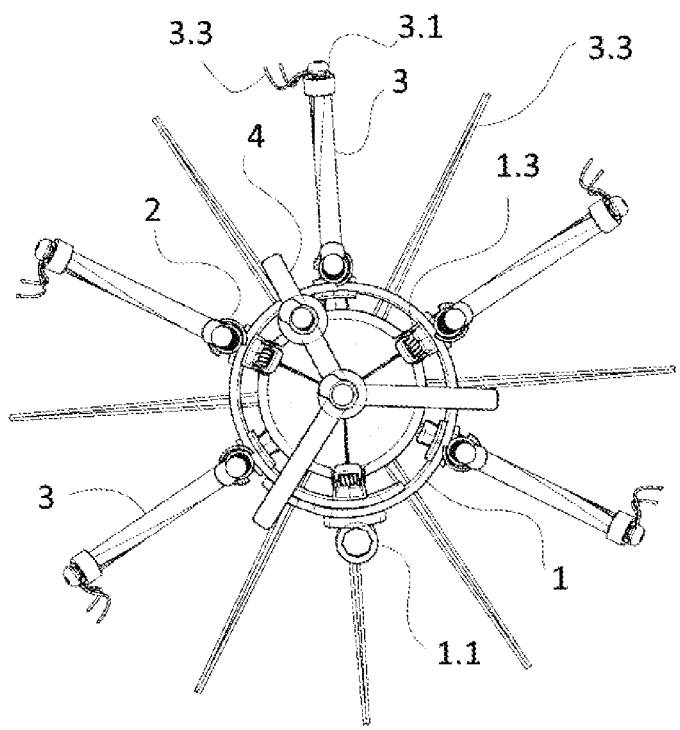

The top view of the invention subject valve sparing aortic root replacement device is illustrated in FIG. 2.

Figure 3:
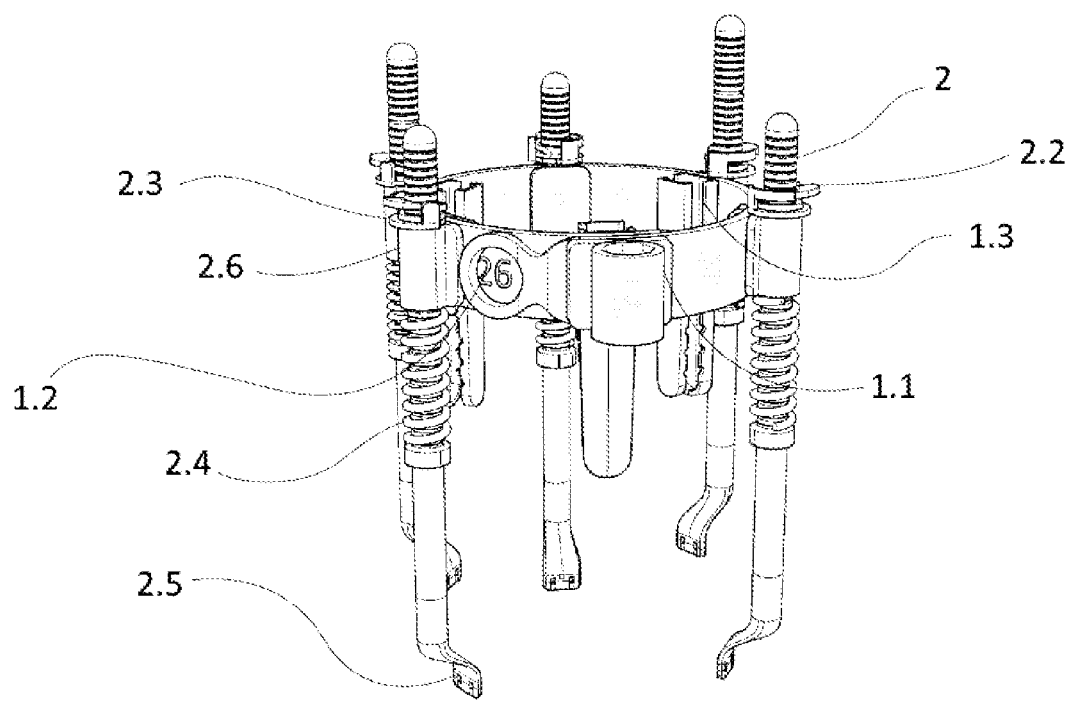

The side view of the invention subject valve sparing aortic root replacement device is illustrated in FIG. 3.

Figure 4:
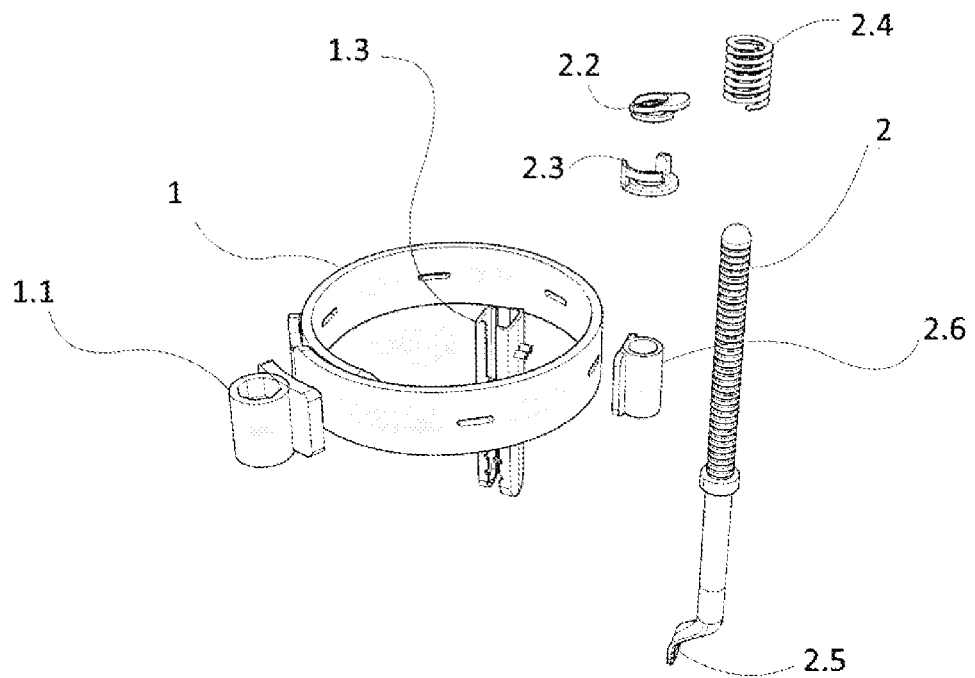

The disassembled view of the invention subject valve sparing aortic root replacement device is illustrated in FIG. 4.

Figure 5:
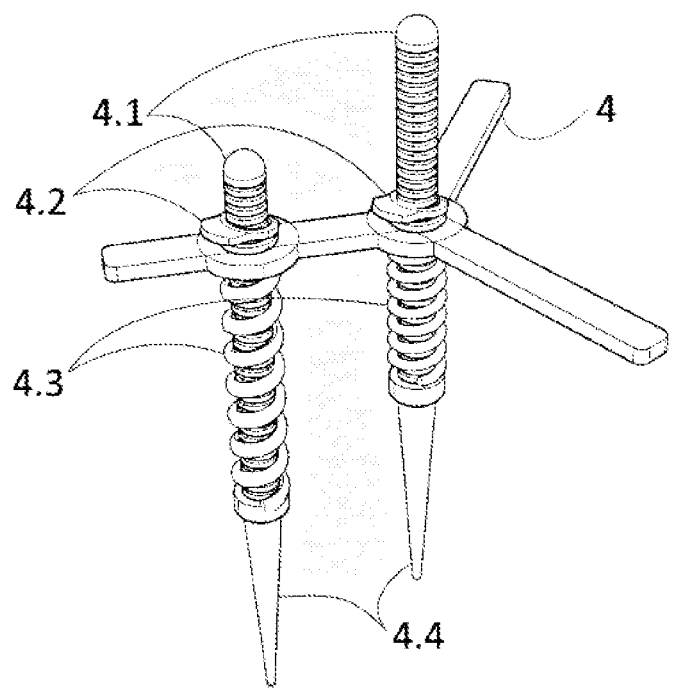

The perspective view of the commissure holders on the invention subject valve sparing aortic root replacement device is illustrated in FIG. 5.

Figure 6:
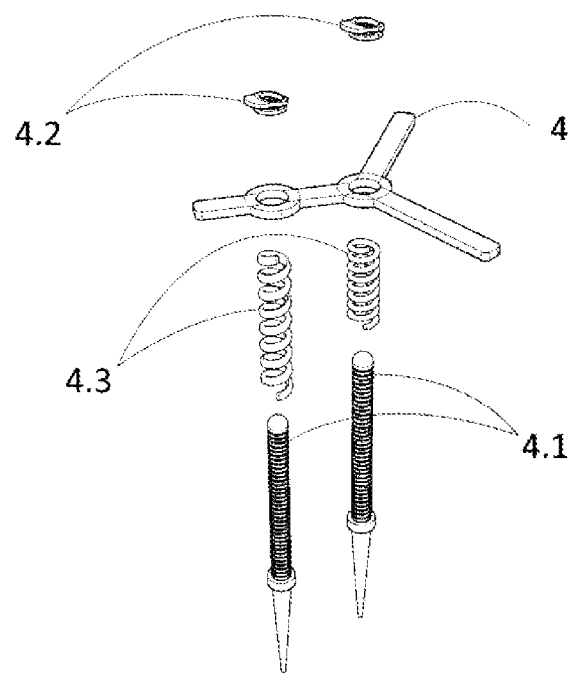

The disassembled view of the commissure holders on the invention subject valve sparing aortic root replacement device is illustrated in FIG. 6.

Figure 7:
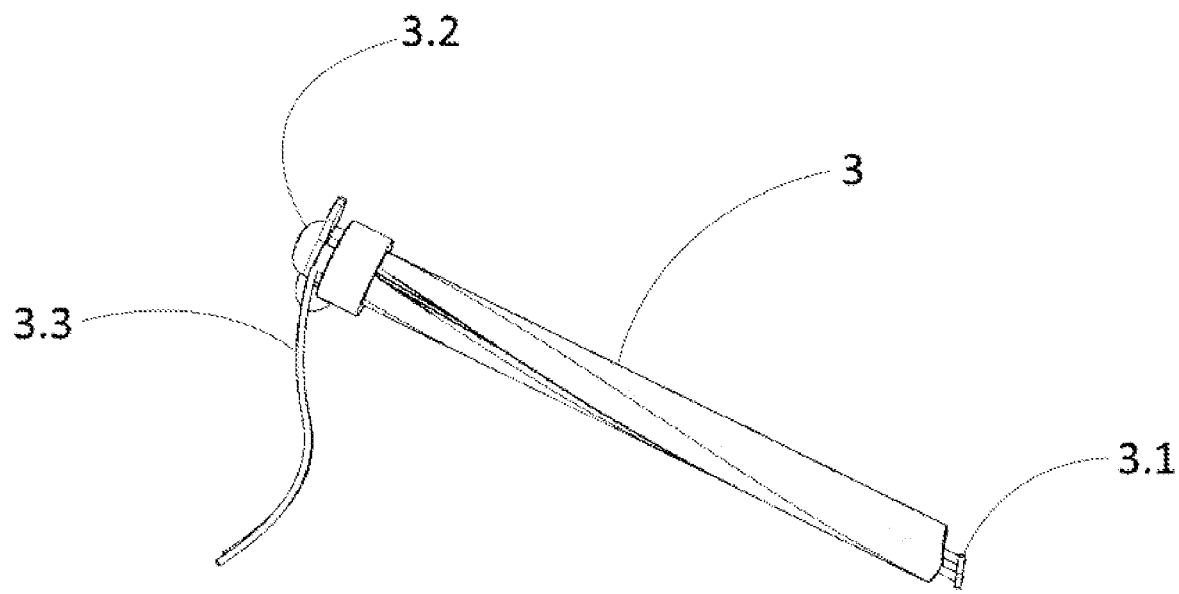

The perspective view of the window showing the graft diameter scale on the invention subject valve protective aortic stem replacement device is illustrated in FIG. 7.

Figure 8:
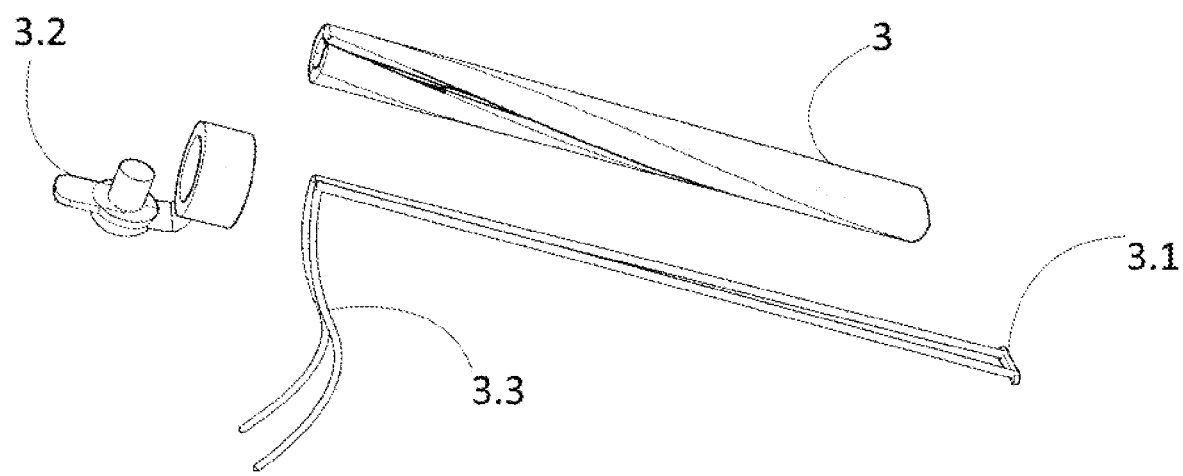

The disassembled view of the window showing the graft diameter scale on the invention subject valve sparing aortic root replacement device is illustrated in FIG. 8.

Figure 9:
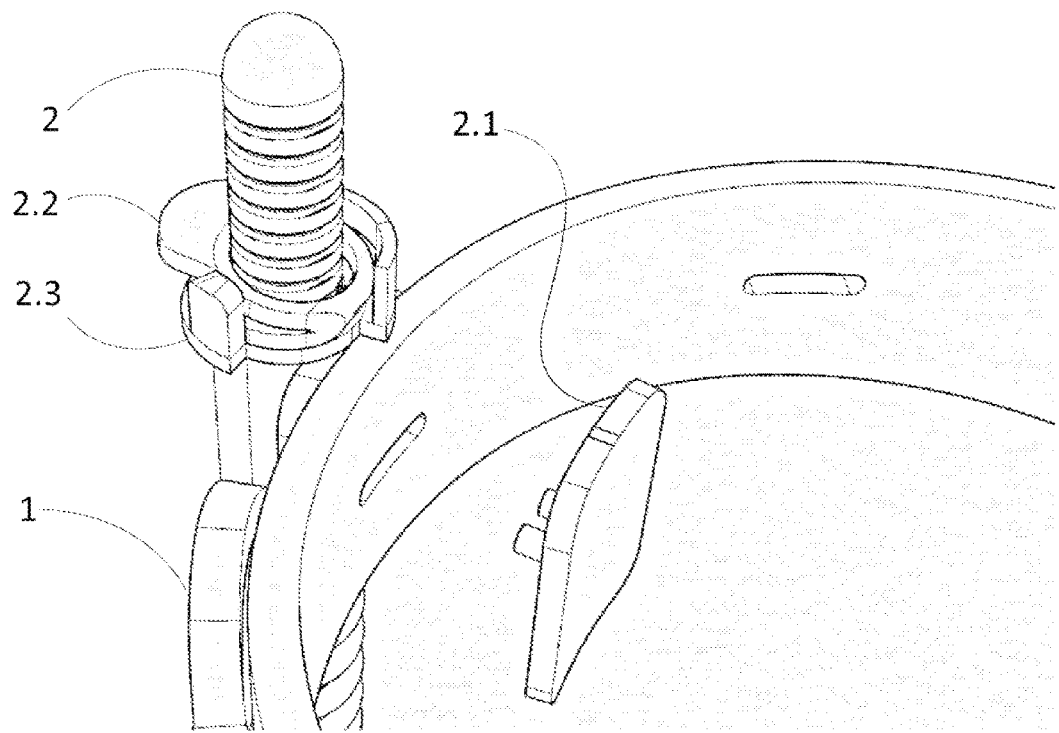

The detailed view of the invention subject valve sparing aortic root replacement device is illustrated in FIG. 9.

Figure 10:
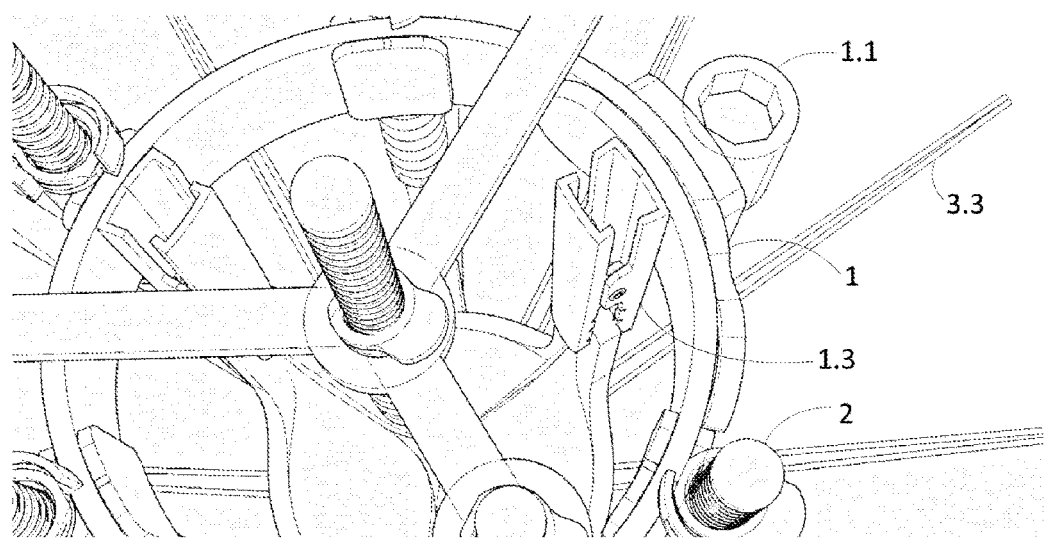

The detailed view of the invention subject valve sparing aortic root replacement device is illustrated in FIG. 10.

Figure 11:
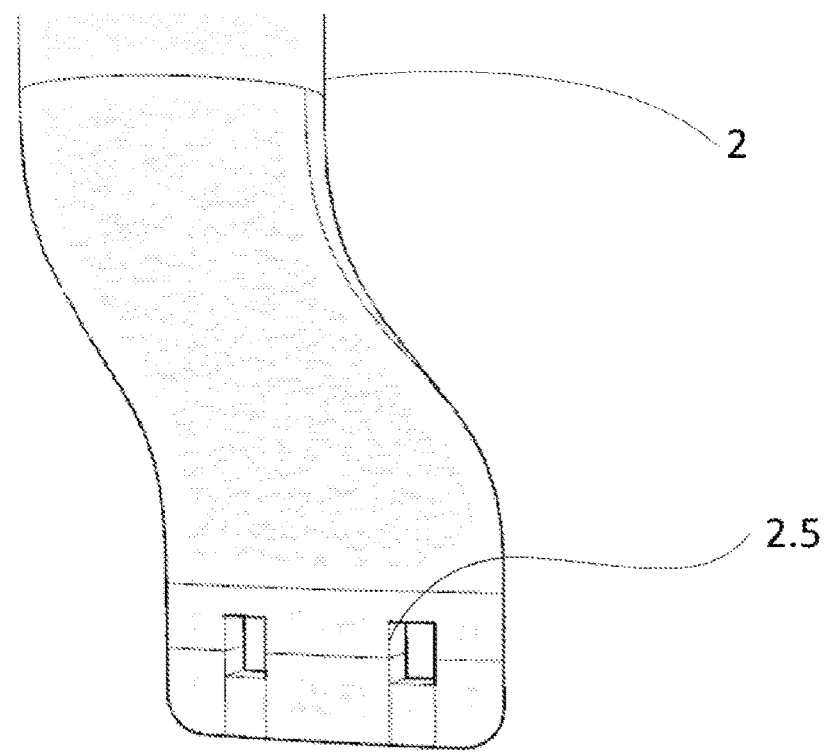

The detailed view of the screw of the adjustable circle on the invention subject valve sparing aortic root replacement device is illustrated in FIG. 11.

Figure 12:
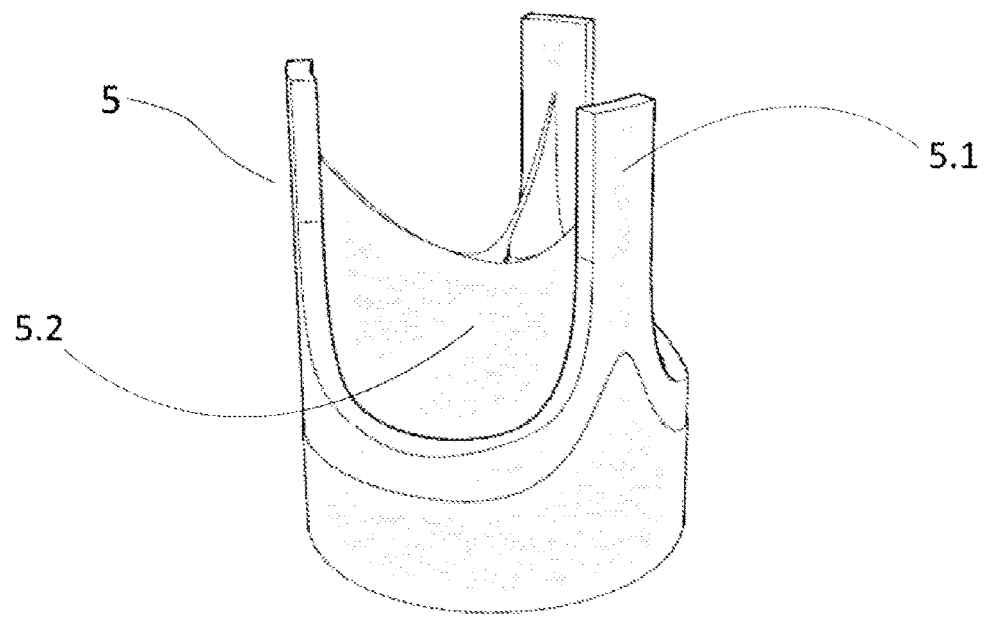

The detailed view of the legs on the invention subject valve sparing aortic root replacement device is illustrated in FIG. 12.

Figure 13:
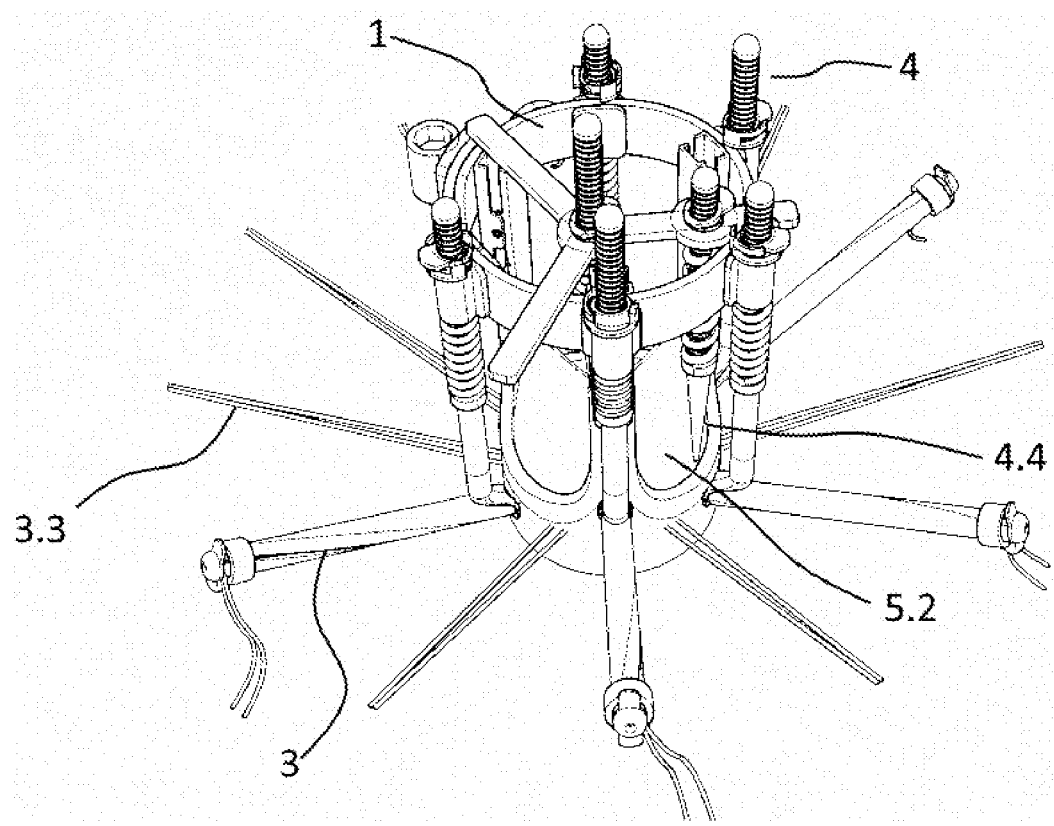

Another perspective view of the invention subject valve sparing aortic root replacement device is illustrated in FIG. 13.

The main parts constituting the invention subject valve sparing aortic root replacement device are: an adjustable circle (1), legs (2), slit surgical tubes (3), cusp caliper (effective height caliper) (4).

The main parts composing the referred adjustable circle (1) are: commissure holders (1.3) clamped to the commissure (5.1) which is the point where the aortic leaflets (5.2) interconnect, circle screw (1.1) that allows for the referred commissure holders (1.3) to approach or move away from each other by changing the diameter of the adjustable-diameter circle (1), and window (1.2) that shows the graft diameter scale, the number written on which at the position where the aortic leaflets (5.2) are positioned at the appropriate value is determined as the diameter of the artificial vessel to be chosen.

The main parts composing the referred legs (2) are: support element (2.1) the convex surface of which sits on the inner surface of the referred adjustable circle (1) and ensures the perpendicular positioning of the legs, leg stabilizer clips (2.2) that fit into the parallel grooves on the legs (2) and ensure fixation, clip stabilizer (2.3) that disables the referred leg stabilizer clips (2.2) and allows the continuous movement of the legs (2), leg springs (2.4) that fulfill the pushing function so as to push the referred adjustable circle (1) from the aortic valve, suture holes (2.5) that ensure the referred legs (2) to stay fixed on the operation suture (3.) that has been tensed by the slit surgical tubes (3), and the leg connectors (2.6) that allows the vertical movement of the adjustable circle (1) on the legs (2).

The main parts composing the referred slit surgical tube (3) are: the operation suture (3.3), surgical teflon pledget (3.1) placed as spongy support material preventing the referred operation suture (3.3) from cutting the tissue, the surgical tube stopper that wraps the output end of the referred operation suture (3.3) from the outside and forms support.

The main parts composing the referred cusp caliper (effective height caliper) (4) are: cusp caliper pins (4.1) that have millimeter scale placed on them, cusp caliper clips (4.2) that fixes the referred cusp caliper pins (4.1), cusp caliper pins (4.1) that perform measurement for each aortic leaflet (5.2) and pin pulling springs (4.3) that fulfill the function of pulling the referred pin endings (4.4).

The main parts composing the referred aortic annulus (5) are: aortic leaflets (5.2) that connect at the center point and form the aortic valve and commissure (5.1) connected as the binary connection places of the referred aortic valves (5.2).

Before the invention subject valve protective aortic root replacement device is placed on the patient, the adjustable circle (1) is brought to the maximum width using the circle screw (1.1). By pressing on the leg stabilizer clips (2.2) on the referred legs (2), each leg stabilizer clips (2.2) is placed in the clip stabilizers (2.3) groove that has been made for it by turning clockwise. The referred leg springs (2.4) push the adjustable-circle (1) so as to move it away from the aortic valve.

The strength of the referred leg springs (2.4) is equal to the force by which the surgeon lifts the aortic leaflets (5.2) by pulling with handle forceps and the suture. In other words, they do not have a suspension force that will make any damages in the tissues.

In this circumstance, the referred legs (2) are in continuously movable position. From the 12 operation sutures (3.3) placed as standard, total 10 needles of the 5 critical operation sutures (3.3) that are always fixed and selected for every patient are passed through the suture holes (2.5) on the 5 legs (2) that correspond to them, and are suspended. The referred surgical teflon pledget (3.1) is positioned as the spongy support material that prevents the operation suture (3.3) from cutting the tissue.

The invention subject valve sparing aortic root replacement device is suspended, and moved to the aortic root as guided by the operation suture (3.3). The referred slit surgical tubes (3) are placed on the referred 5 operation sutures (3.3).

The referred slit surgical tubes (3), are moved through the suture holes (2.5) on the referred legs (2) and the surgical tube stopper (3.2) are closed. Under these circumstances, there are 5 slit siners (3) on the 5 measuring legs (2). But, the referred slit surgical tubes (3) have not yet been tightened.

The referred adjustable circle (1) is slowly contracted and pushed towards the root tissue through the tensing of the operation sutures (3.3) by all slit surgical tubes at the point where the suture holes (2.5) on all legs (2) touch the aortic root tissue. Thus, the 5 legs (2) are fixed between the slit surgical tubes (3) and the root tissue, at the level of the operation suture (3.3).

The referred adjustable circle (1) is pushed towards the aortic root and the commissure holders (1.3) are fixed to the aortic leaflet connections called aortic commissure (5.1).

The referred valve sparing aortic root replacement device is slowly released so that it is positioned. The aortic commissures rise and remain suspended, and at this point, the movement of the device is limited at the point where the referred commissure holders (1.3) suspend the aortic commissures (5.1).

Upon the positioning of the referred valve sparing aortic root replacement device, the leg stabilizer clips (2.2) on each leg (2) are released and it is ensured that each leg (2) is fixed. Now, the aortic valve is suspended with its three-dimensional structure, as it should naturally be.

The central coaptations of the aortic leaflets (5.2) are ensured by narrowing the adjustable circle (1). In this operation that will be made step by step, the height of the aortic leaflet (5.2) (effective height value) is measured over and over again using the cusp caliper (effective height caliper) (4).

When the cusp caliper pins (4.1) of the referred cusp caliper (effective height caliper) are pressed from above, and the pressure is relieved at the moment the pin endings (4.4) touch the aortic leaflets (5.2), the cusp caliper pins (4.1) are fixed at that position. In addition, when the cusp caliper clips (4.2) are pressed, it is ensured that the legs (2) are returned to their initial positions for a new measurement.

The referred pin pulling springs (4.3) operates by pulling the pin endings (4.4). When the cusp caliper clips (4.2) is pressed, the pin endings (4.4) are positioned at the farthest point to the aortic leaflets (5.2), and resume their starting positions for a new measurement.

This measurement is made for each aortic leaflet (5.2) using the pin endings (4.4). The values are taken by the millimeter scale on the cusp caliper pins (4.1).

The process is completed at the moment when this height is 9 mm. Now the effective height that is the most important measurement for the success of the David Procedure has been measured with precise accuracy and the appropriate graft (artificial vessel) diameter is displayed on the window showing the graft diameter scale (1.2).

The referred legs (2) are fixed and, thus show the positions of the 5 operation sutures (3.3). The referred commissure holders (1.3) are opened and the aortic valve structure is released.

The referred surgical tube stoppers (3.2) are opened and the slit surgical tubes (3) are taken off the operation sutures (3.3). The referred device is detached from the operation sutures (3.3) and moved away from the patient.

In this condition, the valve sparing aortic root replacement device holds all the measurements. The graft taken at the diameter indicated by the valve sparing aortic root replacement device is passed through the legs (2) of the device that are in the hand of the surgeon and attached to the commissure holders (1.3) at the same depth (5 mm).

Using a surgical marker pen, the suture holes (2.5) on the legs (2) are marked on the graft.

In addition, the places where the 3 aortic commissures (5.1) will be sutured on the graft are defined by marking the bottom points of the commissure holders (1.3). The graft is removed from the referred device, the other sutures are placed sequentially in between the points marked on the graft.

The referred functional aortic annulus (5) has a 3-dimensional structure. The referred aortic commissure (5.1) and aortic leaflets (5.2) are structures of the referred functional aortic annulus (5).

The referred three aortic commissures (5.1) and the three aortic leaflets (5.2) are connected as binary connection.

As required by the standard operation technique, the referred functional aortic annulus (5) is fully inserted into the artificial vessel (graft). The three commissures (5.1) are suspended in the artificial vessel and sutured. In this way, the three-dimensional structure is reconstructed.

The referred aortic leaflets (5.2) coapt at the center point and form the aortic valve. The referred aortic leaflets (5.2) prevent blood from regurgitating into the heart after the heart has pumped the blood.

The referred support element (2.1) is tightened by the referred leg connectors (2.6). The referred legs (2) move inside the leg connectors (2.6). The tightening strength of the support element (2.1) and the leg connector (2.6) allows horizontal movements inside the groove.

The convex surface of the referred support element (2.1) sits on the inner surface of the adjustable circle (1). The concave surface of the leg connector (2.6) sits on the outside of the adjustable circle. The tightening of the support element (2.1) and the leg holder (2.6) does not prevent the horizontal movements in the groove. However, due to the tight contacts of the 3 curved surfaces with each other, the leg connector (2.6) always remains perpendicular and keeps the legs (2) always perpendicular.

The invention claimed is:

1. A valve sparing aortic root replacement device for use in an operation of valve sparing aortic root replacement for protecting the aortic root of a patient, comprising:
   an adjustable circle configured for being clamped to commissures of the aortic root, the adjustable circle having an adjustable diameter;
   legs configured for allowing placement of the valve sparing aortic root replacement device on the aortic root, the legs being connected to the adjustable circle and being fixable around the aortic root;
   slit surgical tubes configured for holding operation sutures, the slit surgical tubes being further configured for fixing the legs between the slit surgical tubes and the aortic root tissue by means of tensing the operation sutures; and
   a cusp caliper configured for allowing measurement of an aortic leaflet height after the placement of the valve sparing aortic root replacement device on the aortic root.

2. The valve sparing aortic root replacement device according to claim 1, comprising a window displaying a graft diameter scale that defines a diameter of a graft to be chosen based on a position of aortic leaflets after the placement of the valve sparing aortic root replacement device on the aortic root.

3. The valve sparing aortic root replacement device according to claim 1, comprising commissure holders configured for being attached to the commissures of the aortic root.

4. The valve sparing aortic root replacement device according to claim 1, comprising support elements positioned on an inner surface of the adjustable circle, the support elements being configured for ensuring perpendicular positioning of the legs.

5. The valve sparing aortic root replacement device according to claim 1, comprising leg stabilizer clips that fit into grooves on the legs, the leg stabilizer clips being configured for ensuring fixation of the legs in the grooves.

6. The valve sparing aortic root replacement device according to claim 5, comprising clip stabilizers configured for disabling the leg stabilizer clips.

7. The valve sparing aortic root replacement device according to claim 1, comprising leg springs configured for pushing the adjustable circle from the aortic valve in order to lift the aortic leaflets.

8. The valve sparing aortic root replacement device according to claim 1, comprising suture holes configured for ensuring the fixation of the legs at the level of the operation suture tensed by the slit surgical tubes.

9. The valve sparing aortic root replacement device according to claim 1, comprising leg connectors configured for allowing a vertical movement of the adjustable circle on the legs.

10. The valve sparing aortic root replacement device according to claim 1, comprising a surgical teflon pledget configured for preventing the operation suture from cutting the aortic root tissue.

11. The valve sparing aortic root replacement device according to claim 1, comprising a cusp caliper pin having a millimeter scale, the cusp caliper pin being configured for measuring the heights of the lowest and highest levels of the aortic leaflets.

12. The valve sparing aortic root replacement device according to claim 11, comprising a cusp caliper clip configured for fixing the cusp caliper pin.

13. The valve sparing aortic root replacement device according to claim 11, comprising a pin ending configured for performing the measurement by touching the aortic leaflet.

14. The valve sparing aortic root replacement device according to claim 13, comprising a pin-pulling spring configured for pulling the pin ending to an initial position.

15. The valve sparing aortic root replacement device according to claim 1, comprising a circle screw configured for changing the diameter of the adjustable-diameter circle.

* * * * *